United States Patent [19]
Buuck

[11] 3,954,102
[45] May 4, 1976

[54] PENILE ERECTION SYSTEM AND METHODS OF IMPLANTING AND USING SAME

[75] Inventor: Robert E. Buuck, Golden Valley, Minn.

[73] Assignee: American Medical Systems, Inc., Minneapolis, Minn.

[22] Filed: July 19, 1974

[21] Appl. No.: 490,083

[52] U.S. Cl............................................. 128/79; 3/1
[51] Int. Cl.² ............................................ A61F 5/00
[58] Field of Search .................. 128/1, 79, 92 R; 3/1

[56] References Cited
UNITED STATES PATENTS 3,853,122  12/1974  Strauch et al.......................... 128/79

FOREIGN PATENTS OR APPLICATIONS 1,174,814  12/1969  United Kingdom.......... 128/DIG. 25

OTHER PUBLICATIONS
F. B. Scott et al., Urology, July 1973, pp. 80–82.

Primary Examiner—Lawrence W. Trapp
Attorney, Agent, or Firm—Williamson, Bains & Moore

[57] ABSTRACT

The prosthesis comprises a pair of expandable cylinders which are implanted in the penis, replacing the function of the two corpora cavernosa. Supplying fluid to the expandable cylinders is a fluid transfer mechanism that is also implanted in the patient's body so as to permit inflation of the cylinders when an elastomeric bulb is squeezed through the person's skin. In addition to the elastomeric bulb, the fluid transfer system includes a reservoir, a first check valve between the bulb and reservoir, a second check valve between the cylinders and bulb, and a special valve that can be manually operated to by-pass the check valves. In this way, the degree of erection of the penis is controlled by varying the amount of fluid within the prosthetic cylinders by squeezing the elastomeric bulb; deflation is accomplished by actuating the by-pass valve.

8 Claims, 12 Drawing Figures

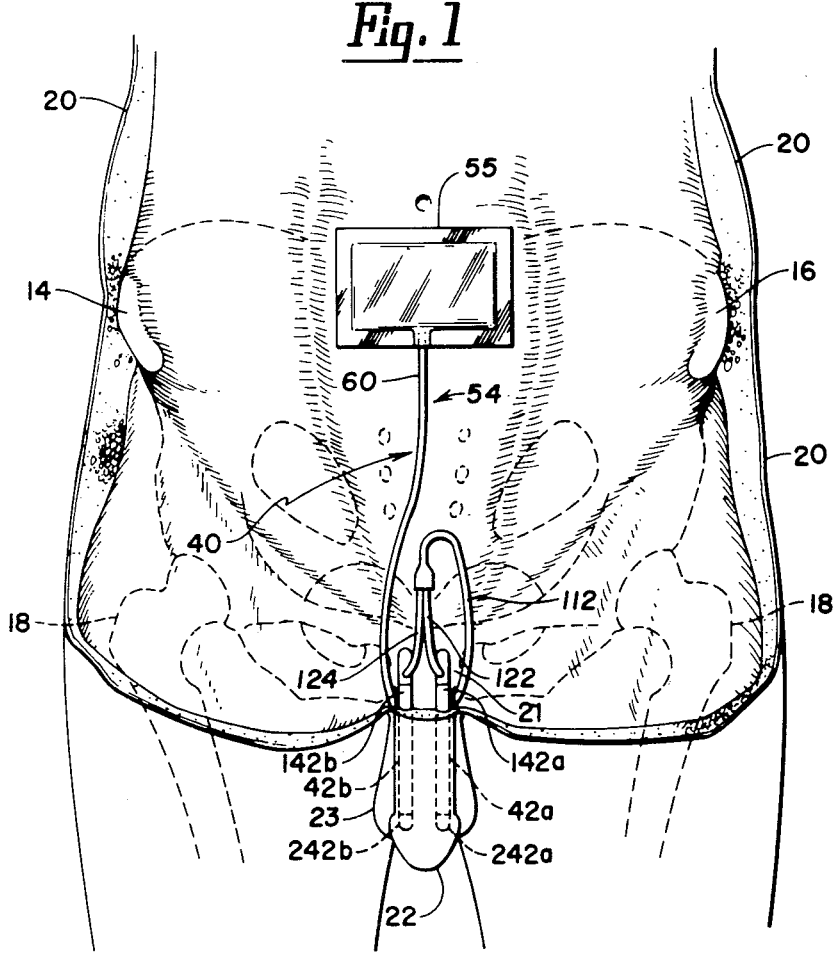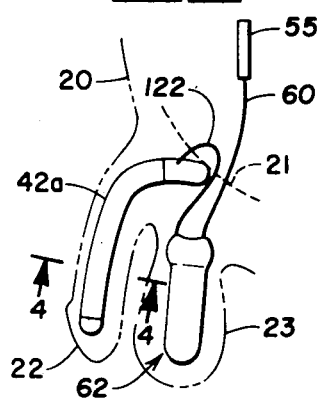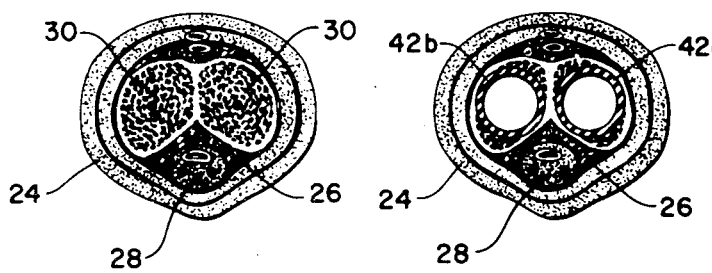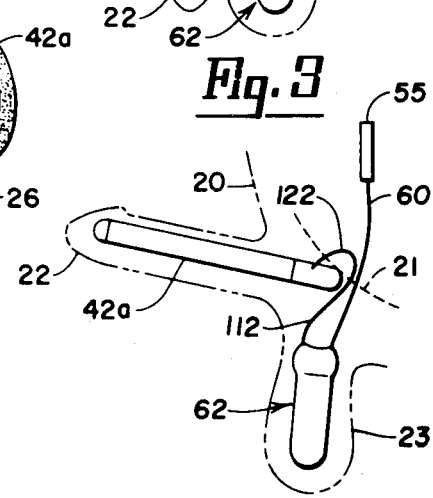

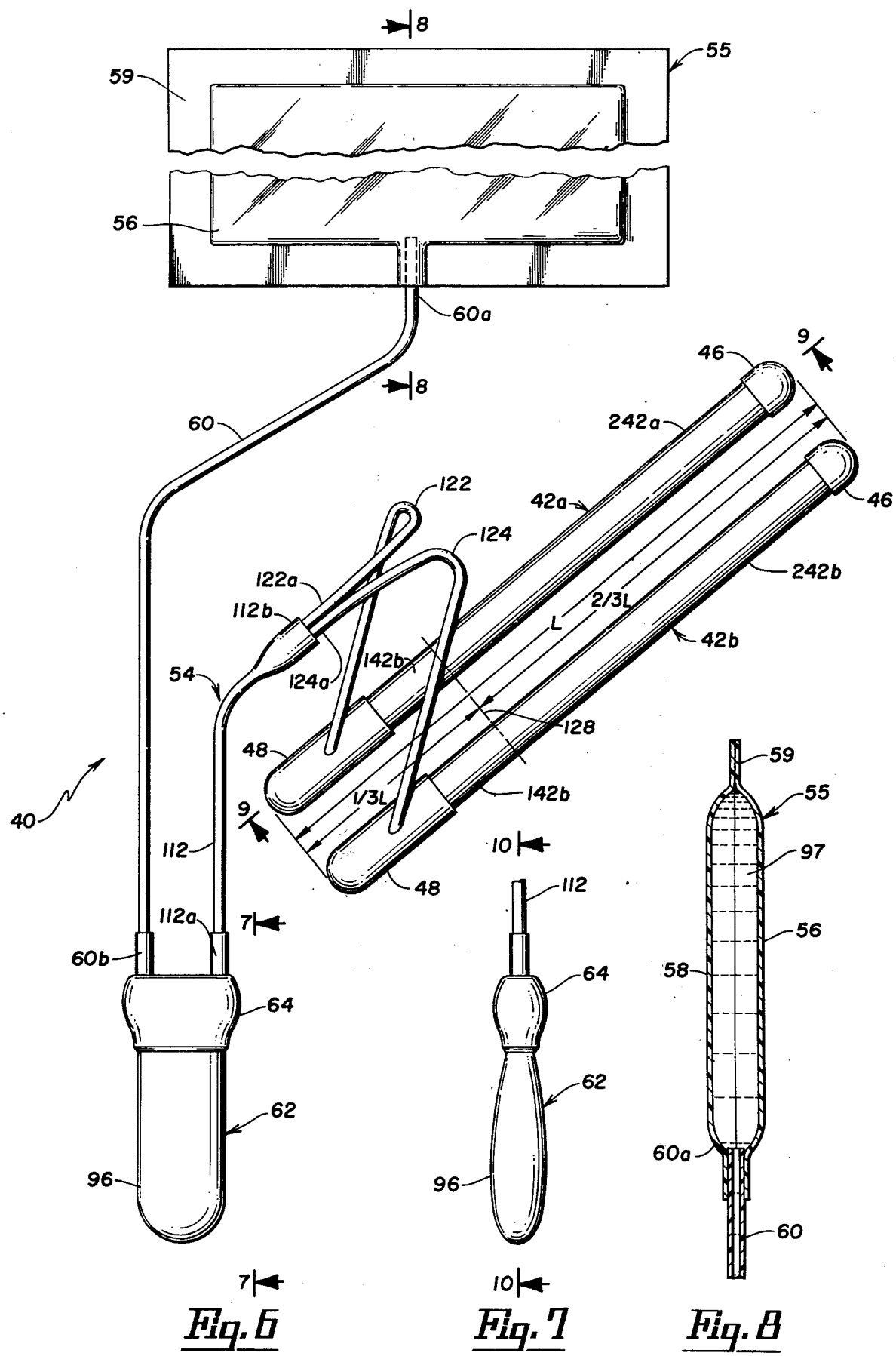

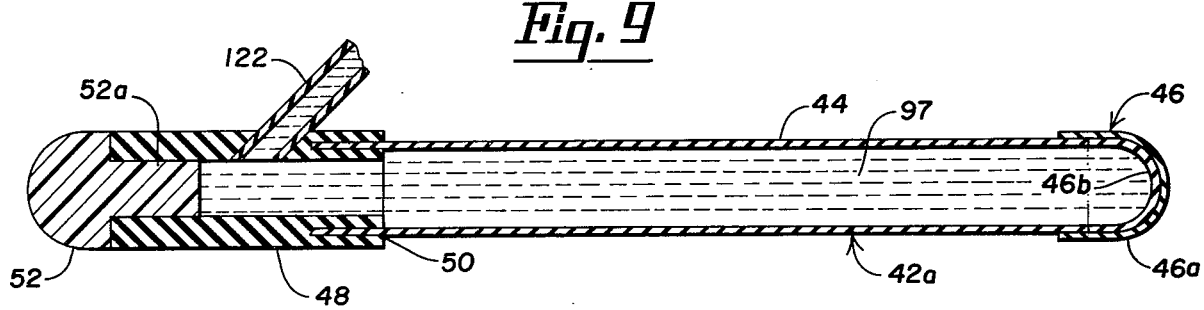
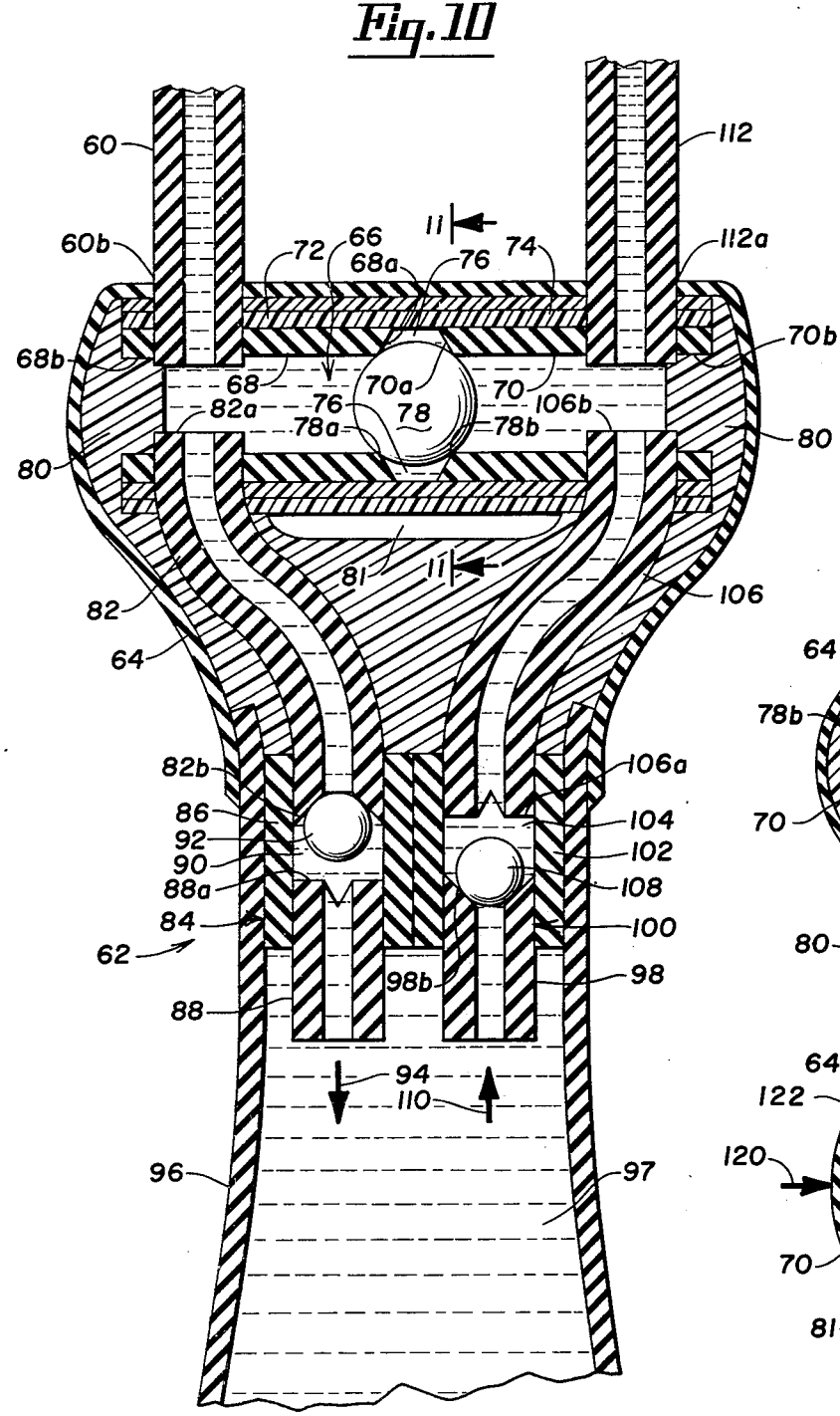
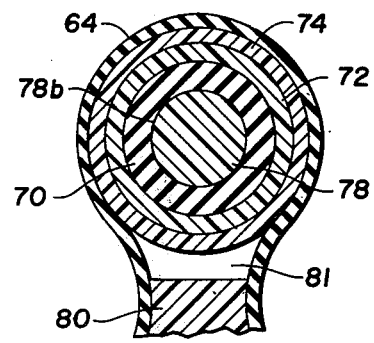
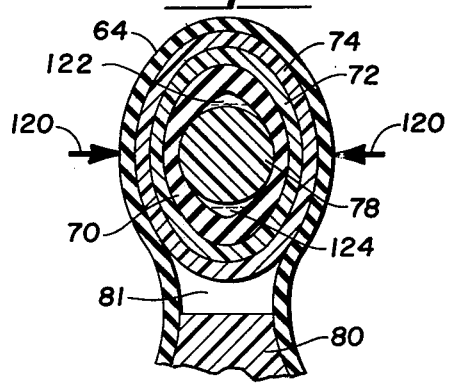

PENILE ERECTION SYSTEM AND METHODS OF IMPLANTING AND USING SAME

BACKGROUND OF THE INVENTION

1. Field of the Invention

This invention relates generally to prosthetic systems, and pertains more particularly to the prosthetic treatment of erectile impotence in the human male.

2. Description of the Prior Art

Present implantable prostheses dealing with treatment of erectile impotence require surgical insertion of a rigid silicone rubber rod into the penis. This approach provides the desired erectile state but is not patient-controllable. In addition, the permanent erectile stage may prove physically uncomfortable or emotionally disconcerting to the patient. Also, the rigid prosthesis has in a number of instances eroded through the skin and falls out of the penis.

SUMMARY OF THE INVENTION

Accordingly, an object of the present invention is to provide a readily controllable penile erection system.

Another object is to avoid physical and emotional discomfort that has attended the rigid rod system mentioned above.

A further object of the invention is to provide a system of the foregoing character in which all components are implanted within the user's body and which are thus totally concealed from view.

Another object of the invention is to provide a system which will achieve the desired result without risking infection, such as is likely to occur when tubes are brought through the skin.

Another object is to provide a system of the above-referred to type that will be physiologically compatible with the person's body tissue and organs. It is also within the purview of the invention to provide a system that is filled with a fluid containing a radiopaque dye that is not only compatible with the material of which the system in constructed but which is also compatible with the body tissues and organs should a leak occur.

A further object of the invention is to provide an implantable system that will not in any way interfere with the performance of other body functions. More specifically, an aim of the invention is to avoid any interference with the passage of either spermatozoa or urine.

Yet another object of the invention is to provide a system that will be simple, compact, long-lasting and which will function without medical supervision once it has been implanted in the body.

Still further, another object is to provide such a system that can be quickly implanted and which will necessitate only a brief hospitalization of the patient.

Briefly, the invention involves the implanting of a self-contained system completely within a human male by replacing the erectile function of the corpora cavernosa of the penis with two inflatable and collapsible cylinders. A fluid transfer system is also implanted in an appropriate portion of the body, such as the lower portion of the patient's abdominal cavity. Included in the system is an elastomeric control bulb located innerjacent the skin, such as within the scrotum, so that the bulb can thereafter be manipulated or squeezed through the skin to force inflating fluid into the cylinders to provide an erection of the penis. A manually operable by-pass valve enables the patient to withdraw fluid so that the penis returns to its normal flaccid condition. Selection of silicone rubber as the material of which the system is constructed plus the use of a fluid containing a radiopaque dye therein that is compatible with the silicone rubber (and also the body tissue and organs) assures that the system will in turn be completely compatible with the body tissue and organs, both as to the material from which it is fabricated and also as far as the fluid is concerned in case there should develop a leak. Also, the employment of a radiopaque dye affords a ready means of determining where the leak has occurred and also the magnitude of any such leak, thereby localizing and thus minimizing the extent of surgical repair.

DESCRIPTION OF THE DRAWINGS

FIG. 1 is a front sectional view depicting the trunk of a male patient having the erectile system implanted therein, the penis appearing in solid outline with the portions of the expandable cylinders implanted therein appearing in phantom outline;

FIG. 2 is a highly diagrammatic side elevational view of the expandable cylinder located toward the left of the penis shown in only phantom outline, the cylinder being only partially filled with fluid resulting in a flaccid condition of the penis;

FIG. 3 is a diagrammatic view corresponding to FIG. 2 but with additional fluid pumped into the particular cylinder that has been depicted to thereby cause the penis to assume an erect state;

FIG. 4 is a pictorial cross sectional view of a penis equipped with prosthetic cylinders that have been implanted in accordance with the teachings of the invention, the view being taken in the direction of line 4—4 of FIG. 2;

FIG. 5 is a cross sectional view corresponding to FIG. 4 but illustrating a penis as it appears prior to implantation of the expandable cylinders used in the practicing of the invention;

FIG. 6 illustrates my system prior to being implanted in a male, the view being as though the parts were laid on a flat table or planar surface for inspection and not in the relation they assume when implanted;

FIG. 7 is a side elevational view of the inflate-deflate unit, the view being taken in the direction of line 7—7 of FIG. 6;

FIG. 8 is a sectional view taken in the direction of line 8—8 of FIG. 6 for the purpose of illustrating one construction the reservoir of my system may assume;

FIG. 9 is a sectional view of one of the expansible cylinders, the view being taken in the direction of line 9—9 of FIG. 6;

FIG. 10 is a sectional view taken in the direction of line 10—10 of FIG. 7 for the purpose of illustrating the internal construction of the inflate-deflate unit;

FIG. 11 is a sectional view of the by-pass valve contained in the inflate-deflate unit, the view being taken in the direction of line 11—11 of FIG. 10, and FIG. 12 is a sectional view corresponding to FIG. 11, but with the by-pass valve flexed to permit passage of fluid.

DESCRIPTION OF THE PREFERRED EMBODIMENT

Referring first to FIG. 1, the trunk of a human male has been denoted generally by the reference numeral 10. Within the pelvic cavity 12 are the right and left hip bones 14, 16 and, for the sake of completion, upper ends of the thigh bones 18 have also been illustrated. The person's skin has been assigned the reference numeral 20, and in FIGS. 2 and 3 the pubic symphysis 21 appears, being depicted only diagrammatically in phantom outline. The reference numeral 22 represents the male's penis and the numeral 23 the scrotum, which parts have been superimposed on FIGS. 2 and 3 in only phantom outline.

It may be helpful to refer generally to the more pertinent parts of the penis 22 as far as this invention is concerned. For this reason, FIG. 5 has been presented. It will be understood, though, that numerous medical textbooks show the parts depicted in FIG. 5 with greater clarity and can be resorted to if necessary; one such textbook is "Gray's Anatomy". At any rate, the penis appearing in cross section in FIG. 5 has the usual outer layer of skin 24, the tissue and blood vessels confined therewithin being designated generally by the numeral 26, the corpus spongiosum 28 and the corpora cavernosa 30. As will be presently explained, the tissue in the corpora cavernosa is collapsed in order to provide space within the penis for the implanting of certain parts in accordance with the invention.

At this time it will be mentioned that the erectile system has been designated generally by the reference numeral 40. Assuming first that the corpora cavernosa have been collapsed, attention is directed to FIG. 4 which shows as a portion of the system 40 a pair of expansible cylinders 42a, 42b that are to perform the function of the corpora cavernosa. Although these cylinders 42 are of identical construction, they have been distinguished from each other by the suffix a and b.

More specifically, each cylinder 42 includes a cylindrical silicone rubber body or sleeve 44 (FIG. 9) which, owing to its resiliency, is expansible circumferentially and also longitudinally. The invention however, is primarily concerned with the ability of each sleeve to expand in length. The body is closed at one end by a rounded rubber cap 46, preferably comprised of two layers 46a, 46b reinforced with polyester fibers (Dacron). As can be seen in FIG. 6, the outer layer 46b overlaps the end of the sleeve or body 44, being secured thereto by means of an implantable grade of adhesive, such as Type A adhesive manufactured by Dow Corning Corporation of Midland, Michigan. At the other end of the body or sleeve 44 is a tube 48, which is about 2.5 cm long, having an annular slit at 50 in which the end portion of the body or sleeve 44 is fitted in a fluid-tight relationship. The wall thickness of the tube 48 is sufficiently great (on the order of 0.35mm) to permit this. The otherwise open end of the tube 48 is closed by means of a plastic plug 52 preferably comprised of Dow plastic 4210 RTV. A portion 52a of plug 52 axially extends part way into the tube 48 in each instance. While the cylinders 42 can vary in length, the typical range is from approximately 15 centimeters to about 21 centimeters. Consequently, the volume of fluid in each cylinder 42 may vary from about 10 milliliters in the smaller cylinders and to about 50 milliliters in the larger sizes. The internal diameter of the cylindrical body 44 may vary appreciably but for the mentioned volumes, this results in internal diameters on the order of 0.5 to 1.5 cm. The wall thickness of the sleeve or body 44 is not critical, but where surgical quality silicone rubber is employed, a wall thickness on the order of 0.8 mm can be employed. Another elastomeric material besides silicone rubber that can be employed is one of the newer polyurethane materials (Tecna).

It is obvious, it is believed, that the cylinders 42 are implanted lengthwise within the penis 22, actually being to either side of a vertical plane passing through the corpus spongiosum 28. Inasmuch as the embryonically provided corpora cavernosa 30 are at an elevation above the corpus spongiosum 28, the prosthesis cylinders 42 are also located slightly above the corpus spongiosum as well as to either side of the vertical plane that has just been mentioned; this relationship is believed readily apparent from FIG. 4 where the cylinders 42a, 42b have been placed within the corpora cavernosa 30 of FIG. 5. The lengthwise positioning of the cylinders 42 is believed readily apparent from FIGS. 1, 2 and 3.

The system 40 additionally comprises a fluid transfer mechanism indicated generally by the reference numeral 54. The entire fluid transfer mechanism 54 is preferably implanted in the lower portion of the patient's abdominal cavity or the upper portion of the pelvic cavity 12 as illustrated in FIG. 1. From especially FIG. 8 it will be discerned that a reservoir 55 is formed with two flexible panels 56, 58. The marginal edges of the panels form a lap joint 59, being sealed together with a suitable adhesive, such as the Type A adhesive mentioned hereinbefore, so as to prevent leakage from the reservoir. The volumetric capacity of the reservoir 55 is on the order of from 40-50 cubic centimeters. Reservoir 55 can be made from the same material which comprises cylinder bodies 44.

From FIGS. 1 and 6 it can be seen that a tube or conduit 60 extends from the reservoir 55, this tube also being comprised of silicone rubber. An implantable grade of adhesive can be employed to assure a liquid tight connection of the tube 60 with the reservoir 55. Here again the Type A adhesive, manufactured by Dow Corning Corporation of Midland, Michigan is quite satisfactory. As indicated, one end 60a of the tube 60 has communication with the interior of the reservoir 55; the other end 60b of this tube 60 is connected to an inflate-deflate unit denoted generally by the reference numeral 62.

Describing the inflate-deflate unit 62 which is shown in detail in FIG. 10, it includes a casing 64, such as 20 mil silicone rubber, reinforced with polyester fibers. The tube end 60b actually extends through the housing wall 64 into one end of a specially constructed by-pass valve labeled 66. The by-pass valve 66 comprises first and second transverse silicone rubber tubes 68, 70 having their adjacent ends 68a and 70a spaced apart. The tubes 68, 70 are contained within a reinforced wrap around Teflon tube 72, and an outer reinforced tube 74. The ends 68a and 70a, together with the wrap around tube 72, form a chamber 76, in which is confined a solid, preferably Teflon ball 78. More specifically the ends 68a and 70a are beveled or chamfered to form machined valve seats for the ball 78. Close inspection of FIG. 10 will reveal that the size of the ball 78 is related to the beveled ends or seats 68a and 70a (see FIG. 11 also) so that a sealing action normally exists by reason of the annular or circular line contacts at 78a and 78b with the spherical outer surface of the ball 78. A mass 80 of adhesive, such as the earlier-mentioned Type A adhesive, blocks the remote ends 68b, 70b of the tubes 68, 70. The mass generally fills the casing 64, although a void is provided at 81. More will be said hereinafter concerning the by-pass function played by the valve 66 including the void 81 associated therewith.

A relatively short tube 82 has its end 82a in communication with the same end of the valve 66 as does the tube 60, and has its end 82b connected to a first check valve 84. The check valve 84 includes a cylindrical body 86, actually a silicone rubber tube, the end 82b of the tube 82 being sealed within one end of the cylindrical body 86. Another tube 88, even shorter than the tube 82, extends from the check valve 84, having its end 88a cemented within the opposite end of the cylindrical body 86 as can be pictorially understood from FIG. 10. A chamber 90 exists between the end 82b of the tube 82 and the end 88a of the tube 88. Within this chamber 90 is contained a solid, preferably Teflon ball 92 that performs the actual checking function. In furtherance of this checking goal, a close inspection of the end 82b of the tube 82 will reveal that it has a machined valve seat. Here again, this is just a chamfer or beveling of the end to form the seat. The end 88a of the tube 88 is notched or serrated. Owing to the serrated configuration of the end 88a of the tube 88, fluid flow can occur through the check valve 84 only in the direction of the arrow indicated by the numeral 94. More specifically, when fluid forces the ball 92 toward the serrated seat 88a (away from the seat 82b with which the ball 92 is engaged as illustrated in FIG. 10), there will be flow in the direction of the arrow 94 because of the passage permitted by the serrated or notched configuration. On the other hand, the ball 92, when urged against the machined valve seat 82b (this seated condition being illustrated), will block flow in this direction, that is opposite to the arrow 94.

The tube 88 communicates with an elastomeric bulb 96, preferably of silicone rubber and part of the unit 62, thereby constituting an expansible chamber device that functions as a pump or "inflate" bulb. It will be observed that the casing 64 overlaps the bulb 96 in the region of the check valve 74, actually being sealed to the casing 64. Some of the fluid of the system 40 appears in FIG. 10 (and also in FIG. 8), having been assigned the reference numeral 97.

Another tube 98 corresponding in length to the tube 88 conducts fluid 97 from the bulb 96 to a second check valve 100 comprising a cylindrical body 102. A chamber 104 is formed between the end 98b of the tube 98 and the end 106a of a tube 106 corresponding generally in length to the previously mentioned tube 82. As with the check valve 84, the check valve 100 also contains a solid ball 108. In this instance, the end 98b is machined to form a valve seat, whereas the end 106a is serrated or notched so as to permit the flow of fluid 97 into the tube 106. The flow of fluid is indicated by the directional arrow 110.

The other end 106b of the tube 106 is connected with the other end of the by-pass valve 66. There is still another tube 112 that extends from the casing 64, its end 112a having communication with the tube 106. Actually, the tube 112 functions to supply fluid 97 to the cylinders 42. To effect this, the tube 112 has a Y end 112b. Sealed within the end 112b are the ends 112a, 124a of still additional tubes 122 and 124. These tubes 122, 124 serve as input tubes for the cylinders 42, actually entering the rather thick tube 48 in each instance. In other words, their ends 122b, 124b are sealed to the tubes 48 at the ends of the two expansible cylinders 42a, 42b. It is thought that FIG. 6 adequately depicts this arrangement.

As already indicated to some degree, the system 40 is filled, but not completely, with the fluid 97 which contains a radiopaque dye selected to be compatible with the permeability characteristics of silicone rubber and physiologically compatible with the body tissue and organs in the event a leak should develop in the system. Perhaps more importantly, the radiopaque fluid 97 enables "visualization" of the location and orientation of the prosthesis subsequent to implantation. As previously mentioned, some of the fluid 97 appears in FIGS. 8 and 10.

IMPLANTING PROCEDURE

Inasmuch as the system 40 is to be installed completely within the body of the male to be treated, surgical procedures are resorted to. Assuming that the system 40 is to have its fluid transfer mechanism 44 implanted in the trunk 10 as illustrated in FIG. 1, an abdominal incision is made through the skin 20 so as to provide access to the pelvic cavity 12. With the pelvic cavity open, the reservoir 55 and the tube 60 can be placed therein. Depending on where the inflate-deflate unit 62 is to be placed determines the extent of the surgical operation. The optimum location for the unit 62 is in the scrotum 23. The implacement of the unit 62 in the scrotum 23 offers a convenient region as far as the inflating and deflating procedures are concerned, all of which will be better understood when considering a typical operational sequence.

Having made the abdominal incision as mentioned above, a rigid metal rod is inserted into the corpora cavernosa 30 from the base of the penis 22 as exposed by the abdominal incision. The erectile tissue within the corpora cavernosa regions of the penis is displaced by the inserted rod. In this way, space is created for the subsequent insertion of the prosthetic cylinders 42. The prosthetic cylinders, actually individually labeled 42a, 42b, are intentionally fabricated into a shape simulating that of the corpora cavernosa 30 and effectively replace their biological function. Inasmuch as the expansible cylinders 42 are of elastomeric material, namely silicone rubber, an exact fit in the resulting cavity derived from the rod insertions steps is not necessary. All that is needed is that the cylinders 42 become stiff when inflated. Quite obviously, the proper selection of size for the prosthetic cylinders 42 will reduce the amount of pumping action, at least initially, so care should be exercised to provide, at least generally, the proper size relationship.

For the sake of facile explanation, the overall or total length of the cylinders 42 in FIG. 6 have been indicated as having a length L. Still further, a line labeled 128 has been superimposed upon FIG. 6 so that approximately one-third the length of the cylinders 42 appear to one side of the line 128 and two-thirds to the other side of the line 128. To further facilitate the description, the one-third length appearing in FIG. 6 has been denoted by the reference numeral 142a as far as the cylinder 42a is concerned, and the corresponding tubular portion of the cylinder 42b by the reference character 142b. The two-third portions have been denoted by the numerals 242a and 242b, respectively. The tubular portions 142a, 142b extend from the pubic symphysis 21 (FIGS. 2 and 3) and provide means by which the cylinders 42a, 42b are anchored so that the tubular portions 242a, 242b, which reside in the penis 22, act as rigid cantilever beams when inflated. The surgeon initially selects the appropriate overall length L (from 15 cm to 21 cm) and during the implanting procedure makes certain that the portions 142a, 142b reside within the trunk 10 and the portions 242a, 242b within the penis 22.

Either before or after the emplacement of the two cylinders 42, more specifically the portions 242a and 242b, into the penis 22, the inflate-deflate unit 62 can be inserted downwardly into the scrotum 23, the pouch-like configuration of this region readily accommodating the entire unit 62.

Although not illustrated, the various tubes 60, 112, 122 and 124 may make use of connectors so that they are the proper length for the particular implanting operation. In other words, the tubes can initially be longer than necessary and shortened to whatever extent is necessary by merely removing a given length and then rejoining the various ends through the agency of the alluded to connectors.

Once the system 40 is implanted, as outlined above, there is no need for further medical attention unless a leak should occur. Leakage, however, is not apt to take place. It has already been pointed out that the radiopaque dye contained in the fluid 97 enables "visualization" of the orientation of the parts within the system, the visualization obviously being with appropriate detection equipment for the particular type of radiant energy being used and for which the radiopaque dye blocks the passage of such energy. Also, the presence of the dye enables any leakage to be detected.

OPERATION

Assuming that the system 40 has been implanted within the trunk 10 of the male body in the manner appearing in FIG. 1 and that it has been substantially filled with fluid 97, from FIGS. 2 and 3 it will be perceived that the user himself can squeeze the particular bulb 96 through the scrotum skin inasmuch as the inflate-deflate unit 62 has been implanted in the scrotum 23 in this instance. In other words, the innerjacency of the bulb 96 with respect to the scrotum skin enables the user to apply squeezing pressure through the skin (and any intervening tissue such as the Dartus Tunic). Hence, the patient's fingers simply knead or squeeze the bulb 96 to force that portion of the fluid 97 therein under pressure through the check valve 100, the tube 112, the tubes 122 and 124 into the expansible cylinders 42a, 42b. It will be appreciated that the ball 108 readily moves away from the seat 98b, being carried by the flowing fluid 97 against the notched or serrated end 106a which, owing to its configuration, allows the passage of fluid. However, the ball 92, under these circumstances, is forced against the seat 82b to prevent flow back to the reservoir 55 via the tube 60. Stated somewhat differently, the flow can only be in the direction of the arrow 110 at this time.

When the pressure being applied through the scrotum skin, which compresses the bulb 96, is relaxed, then the bulb 96 immediately returns to its normal shape and volume, the resiliency of the silicone rubber constituting this bulb being such as to assure such return. In the process of doing this, however, fluid 97 is drawn from the reservoir 55 through the tube 60, the check valve 84 into the bulb 96. In other words, the ball 92 is moved away from the seat 82b toward the notched or serrated end 88a which allows the fluid to pass by reason of the notched configuration. Flow thus occurs in the direction of the arrow 94. During the return of the bulb 96 to its normal size, the ball 108 is drawn against its seat 98b so that fluid 97 that has already been pumped into the cylinders 42 is not withdrawn.

Therefore, it will be recognized that the bulb 96 functions as an expansion chamber device, the repeated compressing and relaxing thereof producing a pumping of fluid into the expansible cylinders 42. The successively repeated squeezing operation or manipulation of the bulb 96 incrementally increases the pressure within the prosthetic cylinders 42. The resulting expansion or inflation of the cylinders 42, more specifically their rubber bodies 44, quickly eliminates any space within the corpora cavernosa 30 and continued pumping simply stiffens the two cylinders 42a, 42b with a concomitant erection of the penis. It will be appreciated that the patient has full control of the erection process, pumping into the cylinders 42 only enough fluid 97 to provide the desired erection state.

During the foregoing inflation or expansion procedure, the by-pass valve 66 remains closed. More specifically, the ball 78 remains engaged with both the seats 68a and 70a so that no fluid 97 flows through the tubes 70, 68 into the tube 60 and hence back to the reservoir 53. In this regard the contractive force exerted by the tubes 68 and 70, supplemented by the overwrapping 72 and 74, produces the line contact sealing engagement denoted by the reference numerals 78a, 78b.

However, when the inflated or expanded cylinders 42 are to be deflated so as to return them to their normal flaccid condition, all that the patient has to do is to squeeze the casing 64 in the region of the check valve 66, doing so through the upper portion of the scrotum skin in contradistinction to the squeezing in the lower portion thereof when performing the pumping or inflation process.

FIG. 12 represents the deformed or open condition of the by-pass valve 66 when being squeezed laterally in the direction of the arrows 120. It will be appreciated that the internal diameter of the Teflon tube or wrapping 72 is such as to permit inward lateral movement, the seats or ends 68a, 70a riding horizontally inwardly over the curved surface of the ball 78. This, however, results in a vertical deformation with the forming of upper and lower openings or passages 122 and 124, as are discernible in FIG. 12. It is the flow through these openings or passages 122, 124 back to the reservoir 55 that causes the cylinders 42 to be deflated. If desired, manual or squeezing pressure can be applied against the penis 22 with the valve 66 held open, thereby hastening the deflation process and the return to a flaccid or limp condition.

Recapitulating, what occurs by reason of the foregoing operational sequence is that the increase of pressure within the prosthetic cylinders 42 causes them to change from the flaccid state or partially filled condition appearing in FIG. 2 to an erect state or condition as appearing in FIG. 3. In other words, the inflated cylinders 42a, 42b become rigid and the tubular portions 242a, 242b act as cantilever beams to carry the weight of the penis 22, the portions 142a, 142b projecting from the penis 22 into the body 10 so as to provide anchorage of the cylinders 42. With respect to the anchorage of the cylinders 42, it has already been mentioned that the portions 142a, 142b constitute approximately one-third the overall length of the cylinders 42a, 42b. It can be further explained at this stage that the portions 142a, 142b are situated within the body 10, the ends thereof abutting the person's pubic symphysis 21 as schematically indicated in FIGS. 2 and 3. Thus, two thirds of the length of the cylinders 42 are within the penis 22. Consequently, the degree of penile erection is in accordance with the amount of fluid 97 that has been pumped into the prosthetic tubes 42, controlled by varying the amount of fluid within these cylinders 42.

I claim:

1. An erectile system for implanting in a male afflicted with erectile impotence, said system comprising:

a first inflatable cylinder for positioning within a first corpora cavernosa region within the male's penis, said first cylinder adapted to expand circumferentially and longitudinally in response to inflation thereof;

a second inflatable cylinder for positioning within a second corpora cavernosa region within the male's penis, said second cylinder adapted to expand circumferentially and longitudinally in response to inflation thereof;

fluid transfer means for inflating said first and second cylinders by directing fluid thereinto in a first direction to produce a penile erection; said fluid transfer means comprising a manually squeezeable elastomeric pump bulb, said pump bulb including a wall portion; and normally closed, manually actuable bypass valve means in fluid flow communication with said first and second inflatable cylinders and normally preventing backflow of fluid out of said cylinders in a second direction opposite to said first direction, said valve means being selectively operable in response to positive actuation to an open position to release fluid from said cylinders in said second direction to thereby deflate said cylinders when it is desired to end said erection, said bypass valve means located interiorly of said pump bulb, and said bypass valve means actuable to said open position by manual displacement of said wall portion of said elastomeric pump bulb.

2. The system of claim 1 including reservoir means for supplying fluid to said transfer means; and including a first check valve connected between said reservoir and said bulb for permitting fluid flow only in the direction of said bulb, and a second check valve connected between said bulb and said cylinders for permitting fluid flow only in the direction of said cylinders, said by-pass valve means being positioned in a flow path between a first location intermediate said first check valve and said reservoir and a second location intermediate said second check valve and said cylinders.

3. The system of claim 2 in which said bulb, check valves and by-pass valve constitute an implantable inflate-deflate unit.

4. The system of claim 3 including a first tube extending from said reservoir to said first check valve, a second tube extending from said second check valve, a third tube extending from said second tube to one of said cylinders, and a fourth tube extending from said second tube to the other of said cylinders.

5. An erectile system for implanting in a male afflicted with erectile impotence, said system comprising:

a first inflatable cylinder for positioning within a first corpora cavernosa region within the male's penis, said first cylinder adapted to expand circumferentially and longitudinally in response to inflation thereof;

a second inflatable cylinder for positioning within a second corpora cavernosa region within the male's penis, said second cylinder adapted to expand circumferentially and longitudinally in response to inflation thereof;

fluid transfer means for inflating said first and second cylinders by direction fluid thereinto in a first direction to produce a penile erection, said fluid transfer means comprising a manually squeezable, elastomeric pump bulb;

reservoir means for supplying fluid to said transfer means; and normally closed, manually actuable bypass valve means in fluid flow communication with said first and second inflatable cylinders and normally preventing backflow of fluid out of said cylinders in a second direction opposite to said first direction, said valve means being selectively operable in response to positive actuation to an open position to release fluid from said cylinders in said second direction to thereby deflate said cylinders when it is desired to end said erection, said by-pass valve means including a ball and a deformable seat associated with said ball to provide a fluid return flow path between said cylinders and said reservoir when said seat is deformed.

6. The system of claim 5 including a first check valve connected between said reservoir and said bulb for permitting fluid to flow only in the direction of said bulb, and a second check valve connected between said bulb and said cylinders for permitting fluid flow only in the direction of said cylinders, said bypass valve means being positioned in a flow path between a first location intermediates at first check valve and said reservoir and a second location intermediate said second check valve in said cylinders.

7. The system of claim 6 in which said bulb, check valves and bypass valve constitute an implantable inflate-deflate unit.

8. The system of claim 7 including a first tube extending from said reservoir to said first check valve, a second tube extending from said second check valve, a third tube extending from said second tube to one of said cylinders, and a fourth tube extending from said second tube to the other of said cylinders.

* * * * *

UNITED STATES PATENT OFFICE
CERTIFICATE OF CORRECTION

Patent No. 3,954,102　　　　　　　　Dated May 4, 1976

Inventor(s) Robert Enno Buuck

It is certified that error appears in the above-identified patent and that said Letters Patent are hereby corrected as shown below:

In claim 6, line 43, change "intermediates at" to --intermediate said-- first check valve....

In claim 6, line 45, change "in" said cylinders to --and-- said cylinders.

*Signed and Sealed this*

Third *Day of* August 1976

[SEAL]

*Attest:*

RUTH C. MASON
*Attesting Officer*

C. MARSHALL DANN
*Commissioner of Patents and Trademarks*